US00PP22087P2

(12) United States Plant Patent
Egger

(10) Patent No.: US PP22,087 P2
(45) Date of Patent: Aug. 16, 2011

(54) *HEUCHERA* PLANT NAMED 'HAVANA'

(50) Latin Name: ***Heuchera* sp.**
Varietal Denomination: Havana

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/800,259

(22) Filed: May 11, 2010

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu
(74) *Attorney, Agent, or Firm* — Karquist Sparkman, LLP

(57) ABSTRACT

A new and distinct *Heuchera* plant characterized by rose colored flowers in a wand-type inflorescence, small yellow to lime colored leaves, very free flowering on short flower stalks, repeat blooming, and a well branched, small, mounding habit.

1 Drawing Sheet

Botanical denomination: *Heuchera* sp.
Variety designation: 'Havana'.

BACKGROUND OF THE INVENTION

The present invention relates to a new and distinct cultivar of *Heuchera* and given the cultivar name of 'Havana'. *Heuchera* is in the family Saxifragaceae. *Heuchera* 'Havana' originated from a cross between *Heuchera* 796-8, a proprietary non-commercial hybrid, as the seed parent, and *Heuchera* 758-1, a proprietary non-commercial hybrid, as, as the pollen parent.

Compared to the seed parent, *Heuchera* 796-8, the new cultivar has yellow to lime colored leaves rather than purple brown.

Compared to the pollen parent, *Heuchera* 758-1, the new cultivar has yellow to lime colored leaves rather than purple.

There are no similar *Heuchera* on the market.

This new *Heuchera* is uniquely distinguished by:

1. rose colored flowers in a wand-type inflorescence,
2. small, veiled, lime colored leaves,
3. very free flowering on short flower stalks,
4. repeat blooming, and
5. a well branched, small, mounding habit.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The photo shows a ten-month-old plant of *Heuchera* 'Havana' growing in a one gallon container in the greenhouse in Canby, Oreg.

DETAILED PLANT DESCRIPTION

The following is a detailed description of the new *Heuchera* cultivar based on observations taken in June of a three-year-old specimen growing in a one gallon container outside in an open greenhouse in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 5$^{th}$ edition.

Plant:

*Form.*—Basal rosette, herbaceous perennial.
*Hardiness.*—USDA Zone 4 to 9.
*Size.*—21 cm tall from top of the foliage to the ground and 39 cm wide.
*Habit.*—Mounding.
*Vigor.*—Good.
*Number of crowns.*—10.

Leaf:

*Type.*—Simple.
*Arrangement.*—Rosette.
*Shape.*—Broadly ovate to orbicular.
*Lobing/division.*—5 shallow lobes, the terminal the longest, shallow secondary lobes.
*Venation.*—Palmate.
*Margins.*—Broadly crenate.
*Apex.*—Mucronulate.
*Base.*—Cordate, lobes overlapping at the base.
*Blade size.*—Grows to 10 cm long and 9 cm wide.
*Surface texture.*—Glandular on the top and on the bottom.
*Petiole description.*—Grows to 12.5 cm long and 2 mm wide, glandular hairs, Yellow Green 146C and tinted Greyed Red 179A in sun.
*Leaf color.*—Topside, young leaves Yellow Green 144A on margins and around veins with a white veil giving a color closest to Green 139D, bottom side Yellow Green 147C; older leaves lighten to Yellow Green 144A on margins and veins with a yellow white veil closest to Green Yellow 1D, bottom side Yellow Green 145C.

Inflorescence:

*Size.*—Grows to 3 cm wide and 28 cm long.

*Type.*—Congested thyrse.

*Number of flowers per thyrse.*—About 90.

*Number of thyrse.*—About 19 in the first spring flush.

*Size of inflorescence.*—Grows to 11 cm long and 3 cm wide.

*Peduncle.*—About 20 cm long, 3 mm wide at base, Greyed Orange 177A, glandular hairs, usually with no cauline leaves.

*Pedicel.*—Variable in size, with glandular hairs, Greyed Orange 177A.

*Bloom period.*—May through June with sporadic rebloom until September in Canby, Oreg.

Flower bud:

*Size.*—2 mm wide and 5 mm long.

*Description.*—Glandular puberulent, narrow ovoid.

*Color.*—Red 53B.

Flower:

*Type.*—Perfect.

*Shape.*—Campanulate.

*Size.*—5 mm long and 5 mm wide.

*Corolla description.*—5 petals, 2 mm long and 1 mm wide, broadly spatulate, glabrous on both sides, acute tip, attenuate base, bottom half entire, top half shallowly crenate, topside Red 54D, bottom side Red 54B.

*Calyx description.*—Campanulate, 6 mm long and 6 mm wide, with 5 lobes flared and divided ½ way to the base, each 3 mm wide and 3 mm long, ovate, glandular hairs inside and outside, tips acute, margin entire with occasional teeth; lobe tips Red Purple 59B inside and out, lobe bases 59C, tube inside and outside 59D.

*Stamen description.*—5 in number, filaments 2 mm long, White NN155C, anthers 0.4 mm, undehisced Red Purple 59C, no pollen, male sterile.

*Pistil description.*—1, 2-beaked, 4 mm long; ovary 2 mm long, Green Yellow 1C; style 2 mm long, White NN155C.

*Fragrance.*—None.

*Lastingness.*—Each thyrse blooms for about 3 weeks on the plant.

No fruit or seed, female sterile:

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

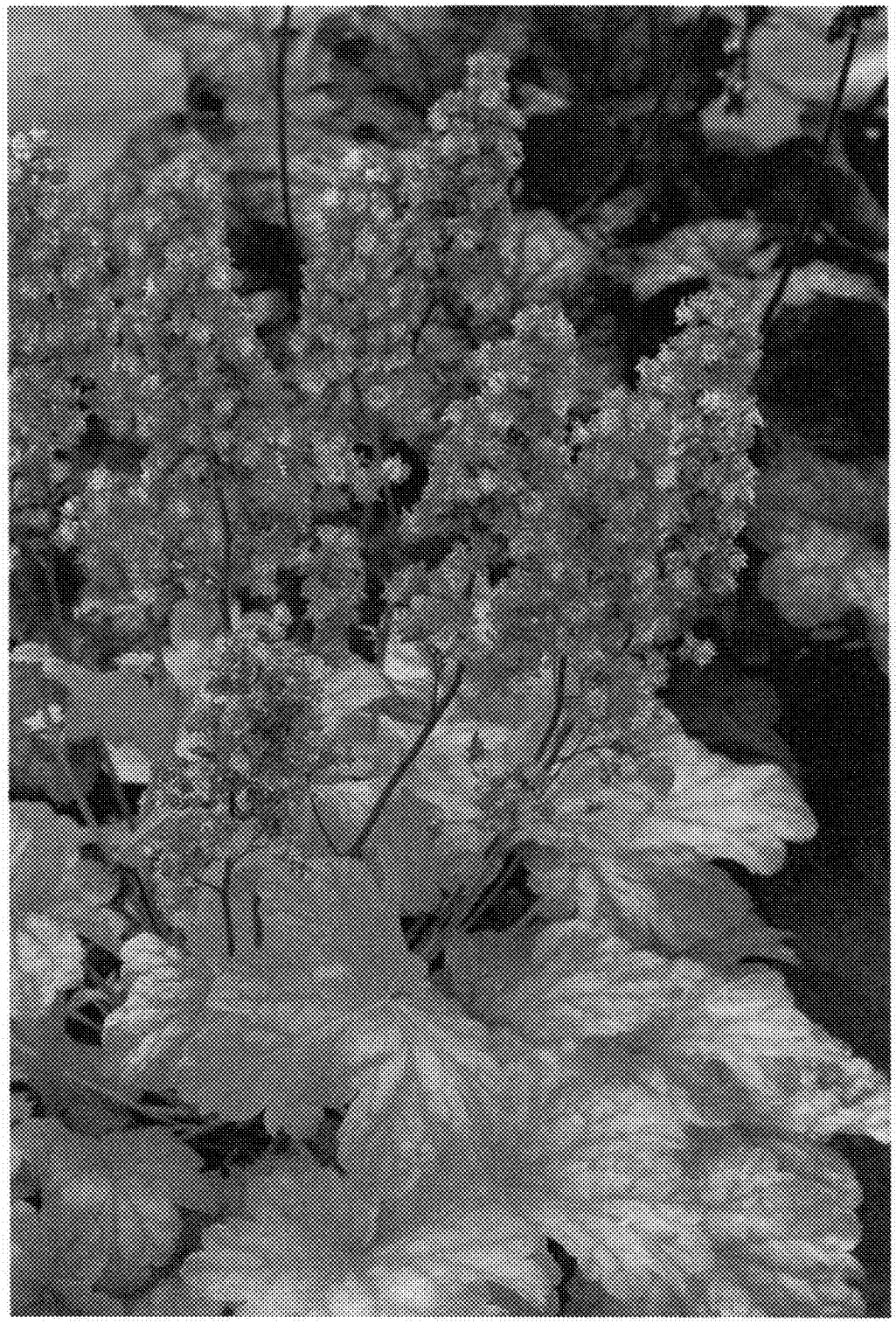

* * * * *